(12) United States Patent
Tateno et al.

(10) Patent No.: US 10,539,553 B2
(45) Date of Patent: Jan. 21, 2020

(54) METHOD AND KIT FOR DETECTING STEM CELL

(71) Applicants: NATIONAL INSTITUTE OF ADVANCED INDUSTRIAL SCIENCE AND TECHNOLOGY, Tokyo (JP); FUJIFILM WAKO PURE CHEMICAL CORPORATION, Osaka (JP)

(72) Inventors: Hiroaki Tateno, Ibaraki (JP); Masaki Warashina, Hyogo (JP); Masakazu Fukuda, Hyogo (JP); Kazunari Hirayasu, Hyogo (JP)

(73) Assignees: NATIONAL INSTITUTE OF ADVANCED INDUSTRIAL SCIENCE AND TECHNOLOGY, Tokyo (JP); FUJIFILM WAKO PURE CHEMICAL CORPORATION, Osaka (JP)

( * ) Notice: Subject to any disclaimer, the term of this patent is extended or adjusted under 35 U.S.C. 154(b) by 11 days.

(21) Appl. No.: 15/548,921

(22) PCT Filed: Dec. 21, 2015

(86) PCT No.: PCT/JP2015/085685
§ 371 (c)(1),
(2) Date: Aug. 4, 2017

(87) PCT Pub. No.: WO2016/147514
PCT Pub. Date: Sep. 22, 2016

(65) Prior Publication Data
US 2018/0038847 A1 Feb. 8, 2018

(30) Foreign Application Priority Data
Mar. 17, 2015 (JP) ................... 2015-053802

(51) Int. Cl.
*G01N 33/53* (2006.01)
*G01N 33/50* (2006.01)
(Continued)

(52) U.S. Cl.
CPC .......... *G01N 33/5073* (2013.01); *C07H 5/04* (2013.01); *G01N 33/57484* (2013.01)

(58) Field of Classification Search
None
See application file for complete search history.

(56) References Cited
U.S. PATENT DOCUMENTS 9,279,809 B2 * 3/2016 Tateno ............. G01N 33/56966
9,500,650 B2 * 11/2016 Tateno ............. G01N 33/56966
(Continued)

FOREIGN PATENT DOCUMENTS

CN 1761749 A 4/2006
CN 102216445 A 10/2011
(Continued)

OTHER PUBLICATIONS

Itakura et al. ("Podocalyxin-Targeting Comparative Glycan Profiling Reveals Difference between Human Embryonic Stem Cells and Embryonal Carcinoma Cells". J Glycomics Lipidomics S5: 004, published Feb. 8, 2013) (Year: 2013).*
(Continued)

*Primary Examiner* — Tracy Vivlemore
*Assistant Examiner* — Nam P Nguyen
(74) *Attorney, Agent, or Firm* — Pearne & Gordon LLP

(57) ABSTRACT

Provided is a method for detecting a stem cell based on an undifferentiated sugar chain marker having a specific sugar chain structure, wherein the stem cell is detected by detecting podocalyxin contained in a culture supernatant or a lysate of cells by a "lectin-antibody sandwich method" using a combination of a lectin and an antibody and having high sensitivity, the method including steps of: contacting the culture supernatant or the lysate, a lectin capable of binding to a sugar chain represented by (Formula 1) or (Formula 2), and an antibody capable of binding to keratan sulfate to form a complex composed of the lectin, podocalyxin and the antibody; and detecting the complex.

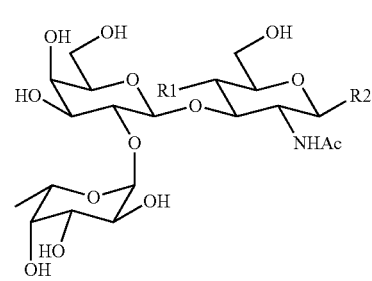

[Formula 1]

wherein R1 represents an OH group or any sugar chain and R2 represents an OH group or any sugar chain, protein, lipid, or another molecule.

[Formula 2]

(Continued)

wherein R1 represents an OH group or any sugar chain and R2 represents an OH group or any sugar chain, protein, lipid, or another molecule.

16 Claims, 4 Drawing Sheets

Specification includes a Sequence Listing.

(51) Int. Cl.
*C07H 5/04* (2006.01)
*G01N 33/574* (2006.01)

(56) References Cited

U.S. PATENT DOCUMENTS

| | | | |
|---|---|---|---|
| 2004/0058395 | A1 | 3/2004 | Hara |
| 2006/0166214 | A1 | 7/2006 | Kato et al. |
| 2011/0171183 | A1 | 7/2011 | Choo et al. |
| 2012/0065089 | A1* | 3/2012 | Kuno ............. G01N 21/648 506/9 |
| 2015/0111218 | A1 | 4/2015 | Tateno et al. |
| 2015/0204870 | A1* | 7/2015 | Tateno ............. G01N 33/56966 435/7.94 |
| 2015/0344567 | A1 | 12/2015 | Kawasaki et al. |

FOREIGN PATENT DOCUMENTS

| | | |
|---|---|---|
| CN | 103987855 A | 8/2014 |
| EP | 1336845 A1 | 8/2003 |
| EP | 2774994 A1 | 9/2014 |
| EP | 2821498 A1 | 1/2015 |
| JP | 2008-122410 A | 5/2008 |
| JP | 2013-039043 A | 2/2013 |
| WO | 2012/147992 A1 | 11/2012 |
| WO | 2013/065302 A1 | 5/2013 |
| WO | WO-2013065302 A1 * | 5/2013 |
| WO | 2013/128914 A1 | 9/2013 |
| WO | 2014/098243 A1 | 6/2014 |

OTHER PUBLICATIONS

Extended European Search Report issued in application No. 15885606.2, dated Sep. 10, 2018, 7 pages.

International Search Report issued in Patent Application No. PCT/JP2015/085685 dated Feb. 23, 2016.

Nielsen, J. et al, "The Role of Podocalyxin in Health and Disease", J Am Soc Nephrol, 2009, vol. 20 No. 8, pp. 1669-1676.

Sulak, O. et al, "A TNF-like Trimeric Lectin Domain from Burkholderia cenocepacia with Specificity for Fucosylated Human Histo-Blood Group Antigens", Structure, Jan. 13, 2010, vol. 18 No. 1, pp. 59-72.

Kawabe, K. et al, "A novel antibody for human induced pluripotent stem cells and embryonic stem cells recognizes a type of keratan sulfate lacking oversulfated structures", Glycobiology, 2013, vol. 23 No. 3, pp. 322-336.

Tateno, H. et al, "Glycome Diagnosis of Human Induced Pluripotent Stem Cells Using Lectin Microarray", Journal of Biological Chemistry, Jun. 10, 2011, vol. 286 No. 23, pp. 20345-20353.

Schopperle, W. et al, "The TRA-1-60 and TRA-1-81 Human Pluripotent Stem Cell Markers Are Expressed on Podocalyxin in Embryonal Carcinoma", Stem Cells, 2007, vol. 25, pp. 723-730.

Badcock, G. et al, "The Human Embryonal Carcinoma Marker Antigen TRA-1-60 Is a Sialylated Keratan Sulfate Proteoglycan", Cancer Research, Sep. 15, 1999, vol. 59, pp. 4715-4719.

Natunen, S. et al, "The binding specificity of the marker antibodies Tra-1-60 and Tra-1-81 reveals a novel bluripotency-associated type 1 lactosamine epitope", Glycobiology, 2011, vol. 21 No. 9, pp. 1125-1130.

Tateno, H. et al, "A medium hyperglycosylated podocalyxin enables noninvasive and quantitative detection of tumorigenic human pluripotent stem cells", Scientific Reports, Feb. 12, 2014, vol. 4 No. 4069, pp. 1-8.

Kawasaki, T. et al, "Working principle and relation with disease and biological phenomena, Novel iPS/ES marker antibodies and application thereof", Experimental Medicine, 2013, vol. 31 No. 10, pp. 1597-1601.

Cosmo Bio Co., Ltd., "Anti-Keratan Sulfate (R-10G) Antibody," 3 pages, https://www.cosmobio.co.jp/connections/p_ku_e_view.asp?PrimaryKeyValue=747740&ServerKey=Primary&selPrice=1, last accessed Jun. 22, 2019.

National Institute of Technology and Evaluation, "International Patent Organism Depositary, NITE (IPOD, NITE)," 2 pages, https://www.nite.go.jp/en/nbrc/patent/pod/idex.html, last accessed Jun. 22, 2019.

Office Action for Chinese Application No. 201580077538.5 dated Jul. 1, 2019.

Tateno et al., "Podocalyxin is a Glycoprotein Ligand of the Human Pluripotent Stem Cell-Specific Probe rBC2LCN", Stem Cells Translational Medicine, vol. 2, pp. 265-273, Apr. 30, 2013.

* cited by examiner

METHOD AND KIT FOR DETECTING STEM CELL

TECHNICAL FIELD

The present invention relates to a method and a kit for detecting a stem cell. More specifically, the invention relates to a method and the like for detecting a stem cell by detecting podocalyxin contained in a culture supernatant or a lysate of cells by a lectin-antibody sandwich method.

BACKGROUND ART

One of the challenges for the regenerative medicine technique using a multipotential stem cell (hereinafter also simply referred to as "stem cell"), such as an induced pluripotent stem cell (iPS cell) or an embryonic stem cell (ES cell), is how to prevent the risk that the stem cell might remain in an undifferentiated state, be transplanted into a patient's body together with its differentiated cell, and be tumorigenically transformed or become cancerous in the patient's body in transplantation into the patient's body after differentiating the stem cell into a desired type of cell.

Patent Literature 1 discloses a method for determining the differentiation status of a stem cell by detecting a sugar chain specific for the cell using a lectin capable of binding to the sugar chain as a technique usable for evaluating the contamination of the undifferentiated stem cell which might have tumorigenicity. This method involves detecting an undifferentiated sugar chain marker having the sugar chain structure of "Fucα1-2Galβ1-3GlcNAc" and/or "Fucα1-2Galβ1-3GalNAc" using a recombinant protein of a lectin called BC2LCN lectin (rBC2LCN lectin). rBC2LCN lectin is a recombinant protein obtained by expressing BC2LCN lectin (GenBank Accession No. YP_002232818) corresponding to the N-terminal domain of BC2L-C protein derived from a gram-negative bacterium (*Burkholderia cenocepacia*) in transformed *Escherichia coli*, and recognizes the above sugar chain structure.

Patent Literature 2 discloses a method for detecting an undifferentiated stem cell remaining after differentiation induction treatment by detecting the above sugar chain in the stem cell culture supernatant using rBC2LCN lectin. Patent Literature 2 has identified a complex carbohydrate, podocalyxin, as an undifferentiated sugar chain marker having the sugar chain structure of "Fucα1-2Galβ1-3GlcNAc" and/or "Fucα1-2Galβ1-3GalNAc".

CITATION LIST

Patent Literature

Patent Literature 1: International Publication No. WO2013/128914
Patent Literature 2: International Publication No. WO2013/065302
Patent Literature 3: International Publication No. WO2012/147992

Non Patent Literature

Non Patent Literature 1: J. Am. Soc. Nephrol., 2009, Vol. 20, No. 8, p. 1669-1676.
Non Patent Literature 2: Structure, 2010, Vol. 18, No. 1, p. 59-72.
Non Patent Literature 3: Glycobiology, 2013, Vol. 23, No. 3, p. 322-336.
Non Patent Literature 4: J. Biol. Chem., 2011, Vol. 286, No. 23, p. 20345-20353.
Non Patent Literature 5: Stem Cells, 2007, Vol. 25, p. 723-730.
Non Patent Literature 6: Cancer Research, 1999, Vol. 59, p. 4715-4719.
Non Patent Literature 7: Glycobiology, 2011, Vol. 21, No. 9, p. 1125-1130.
Non Patent Literature 8: Scientific Reports, 2014, Vol. 4, p. 4069.

SUMMARY OF INVENTION

Technical Problem

The above Patent Literature 2 discloses "sandwich method" for detecting an undifferentiated sugar chain marker by capturing an undifferentiated sugar chain marker in the stem cell culture supernatant by a lectin (rBC2LCN lectin) immobilized on a substrate to form a complex of the lectin and the undifferentiated sugar chain marker and reacting the complex with another labeled lectin or a labeled antibody, as a preferred embodiment.

Patent Literature 2 lists 4 lectins called SRL, CGL2, ABA, and XCL as lectins capable of being provided in "lectin-lectin sandwich method" in combination with rBC2LCN lectin.

The main object of the present invention is to provide a highly sensitive "lectin-antibody sandwich method" using a combination of a lectin and an antibody in a method for detecting a stem cell based on an undifferentiated sugar chain marker (podocalyxin) having the sugar chain structure of "Fucα1-2Galβ1-3GlcNAc" and/or "Fucα1-2Galβ1-3GalNAc".

Solution to Problem

To solve the above problems, the present invention provides the following [1] to [17].

[1] A method for detecting a stem cell by detecting podocalyxin contained in a culture supernatant or a lysate of cells, the method comprising steps of: contacting the culture supernatant or the lysate, a lectin capable of binding to a sugar chain represented by (Formula 1) below:

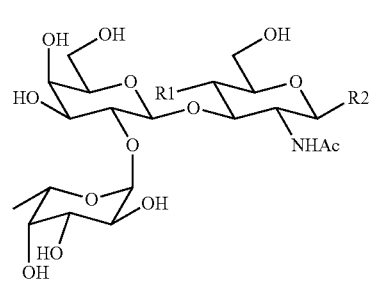

[Formula 1]

wherein R1 represents an OH group or any sugar chain and R2 represents an OH group or any sugar chain, protein, lipid, or another molecule, or (Formula 2) below:

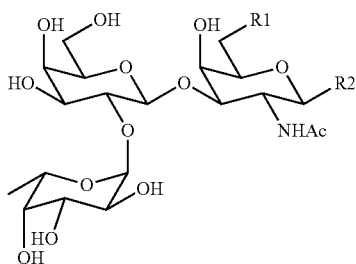

[Formula 2]

wherein R1 represents an OH group or any sugar chain and R2 represents an OH group or any sugar chain, protein, lipid, or another molecule, and
an antibody capable of binding to keratan sulfate
to form a complex composed of the lectin, podocalyxin, and the antibody; and
detecting the complex.

[2] The method according to [1], wherein the antibody is an antibody capable of binding to low-sulfated keratan sulfate.

[3] The method according to [1] or [2], wherein for the antibody, the epitope comprises Gal-GlcNAc (6S) or a tandem repeat thereof.

[4] The method according to any one of [1] to [3], wherein the antibody is an antibody produced by hybridoma R-10G (accession number: FERM BP-11301) or an antibody competing with the antibody.

[5] The method according to any one of [1] to [4], wherein the cells are cells cultured in a serum-containing medium.

[6] The method according to any one of [1] to [5], wherein the lectin is:
a protein comprising the amino acid sequence of SEQ ID NO: 1 or a protein comprising an amino acid sequence in which 1 or several amino acids are deleted, substituted, inserted, or added in the amino acid sequence and being capable of binding to a sugar chain represented by the (Formula 1) or (Formula 2).

[7] The method according to any one of [1] to [6], comprising steps of:
contacting the culture supernatant or the lysate with the lectin to form a first complex composed of the lectin and podocalyxin contained in the culture supernatant or the lysate; and
contacting the first complex with the antibody to form a second complex composed of the lectin, podocalyxin, and the antibody.

[8] The method according to [7], wherein the lectin is bound to an insoluble support.

[9] A method for detecting a stem cell by detecting a sugar chain represented by (Formula 1) below:

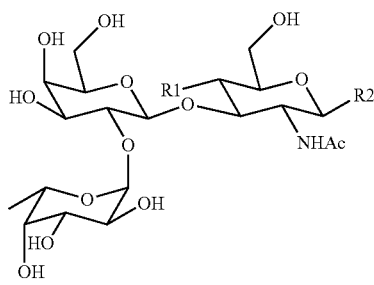

[Formula 3]

wherein R1 represents an OH group or any sugar chain and R2 represents an OH group or any sugar chain, protein, lipid, or another molecule, or (Formula 2) below:

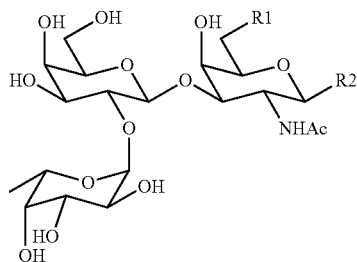

[Formula 4]

wherein R1 represents an OH group or any sugar chain and R2 represents an OH group or any sugar chain, protein, lipid, or another molecule, contained in a culture supernatant or a lysate of cells, the method comprising steps of:
contacting the culture supernatant or the lysate, a lectin capable of binding to the sugar chain, and an antibody capable of binding to keratan sulfate to form a complex comprising the lectin, the sugar chain, and the antibody; and
detecting the complex.

[10] The method according to any one of [1] to [9], further comprising a step of determining the presence or absence or abundance of the stem cell contained among the cells based on the presence or absence or a detected amount of the complex.

[11] The method according to any one of [1] to [9], further comprising a step of determining the differentiation status of the cells based on the presence or absence or a detected amount of the complex.

[12] A method for detecting podocalyxin contained in a culture supernatant or a lysate of cells, the method comprising steps of:
contacting the culture supernatant or the lysate, a lectin capable of binding to a sugar chain represented by (Formula 1) below:

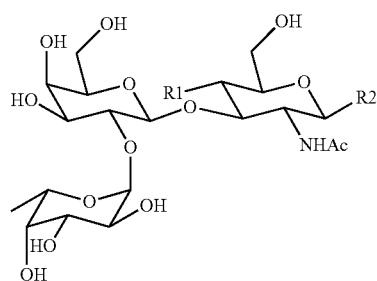

[Formula 5]

wherein R1 represents an OH group or any sugar chain and R2 represents an OH group or any sugar chain, protein, lipid, or another molecule, or (Formula 2) below:

[Formula 6]

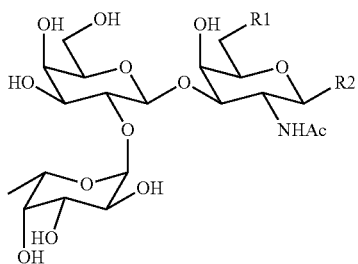

wherein R1 represents an OH group or any sugar chain and R2 represents an OH group or any sugar chain, protein, lipid, or another molecule, and
an antibody capable of binding to keratan sulfate
to form a complex composed of the lectin, podocalyxin, and the antibody; and
detecting the complex.

[13] A kit for detecting a stem cell contained among cells by detecting podocalyxin contained in a culture supernatant or a lysate of the cells, the kit comprising: a lectin capable of binding to a sugar chain represented by (Formula 1) below:

[Formula 7]

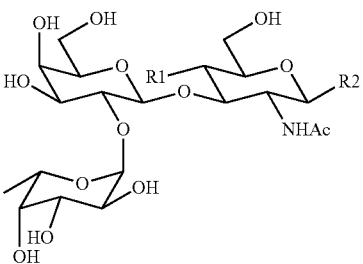

wherein R1 represents an OH group or any sugar chain and R2 represents an OH group or any sugar chain, protein, lipid, or another molecule,
or (Formula 2) below:

[Formula 8]

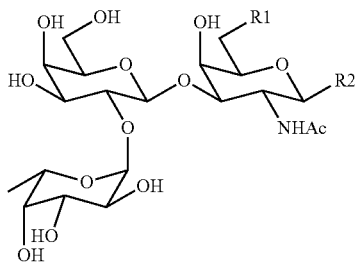

wherein R1 represents an OH group or any sugar chain and R2 represents an OH group or any sugar chain, protein, lipid, or another molecule; and
an antibody capable of binding to keratan sulfate.

[14] The kit according to [13], wherein the antibody is an antibody capable of binding to low-sulfated keratan sulfate.

[15] The kit according to [13] or [14], wherein for the antibody, the epitope comprises Gal-GlcNAc (6S) or a tandem repeat thereof.

[16] The kit according to any one of [13] to [15], wherein the antibody is an antibody produced by hybridoma R-10G (accession number: FERM BP-11301) or an antibody competing with the antibody.

[17] The kit according to any one of [13] to [16], wherein the lectin is bound to an insoluble support.

Podocalyxin is a type 1 transmembrane glycoprotein, identified from an epithelial glomerular cell (podocyte), and known to be associated with the development of various cancers as well as to play important roles in keeping the function and morphology of the glomerulus (see Non Patent Literature 1). For the purpose of the present invention, the term "podocalyxin" encompasses both the full-length protein of podocalyxin and its partial fragment provided that it has the sugar chain structure of the (Formula 1) and/or (Formula 2).

For the purpose of the present invention, the "sugar chain" means a group of compounds each having a structure in which monosaccharides are linked to each other in a chain (straight chain or dendritically branched chain) form by glycosidic linkage. Monosaccharides constituting the sugar chain include hexoses, such as glucose (Glc), galactose (Gal), and mannose; deoxyhexoses, such as L-fucose (Fuc); hexosamines such as N-acetylglucosamine (GlcNAc) and N-acetylgalactosamine (GalNAc); sialic acids, such as N-acetylneuraminic acid and N-glycolylneuraminic acid; and pentoses, such as xylose and L-arabinose. The number of monosaccharides constituting the "sugar chain" is not particularly limited and on the order of 2 to several tens of thousands.

For the purpose of the present invention, the "lectin" means a protein recognizing, and binding to, the partial structure or the whole structure of the sugar chain binding to a complex carbohydrate, such as a glycoprotein, a glycolipid, a proteoglycan, a glycopeptide, a lipopolysaccharide, a peptidoglycan, and a glycoside of a steroid compound or the like.

Advantageous Effects of Invention

According to the present invention, a highly sensitive "lectin-antibody sandwich method" using a combination of a lectin and an antibody is provided in a method for detecting a stem cell based on an undifferentiated sugar chain marker (podocalyxin) having the sugar chain structure of "Fucα1-2Galβ1-3GlcNAc" and/or "Fucα1-2Galβ1-3GalNAc".

DESCRIPTION OF EMBODIMENTS

Figure 1:
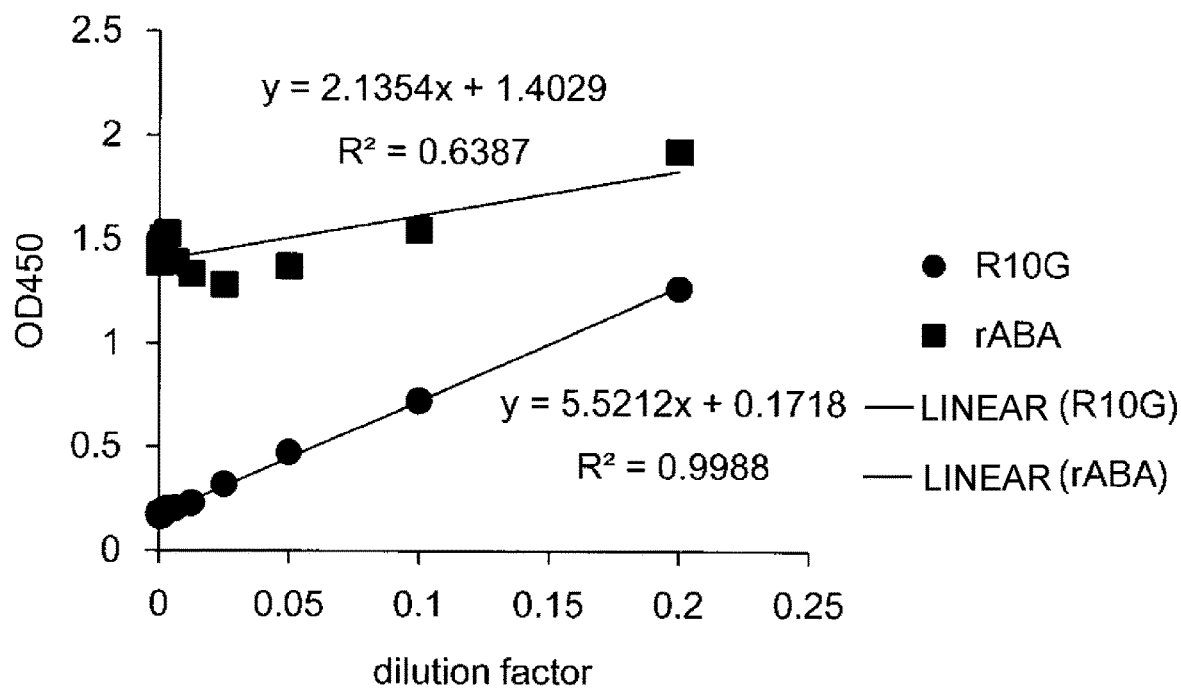
FIG. 1 is a graph showing the results of evaluating the method for detecting stem cells by the lectin-antibody sandwich method according to the present invention by comparison with that by the lectin-lectin sandwich method according to the conventional art (Test Example 1).

Preferred embodiments for carrying out the present invention will be described below. The embodiments described below are intended only to show an example of an exemplary embodiment of the present invention, but the scope of the present invention is not intended to be construed in a limiting sense thereby.

1. Method for Detecting Stem Cell

The method for detecting a stem cell according to the present invention involves detecting a stem cell by detecting a sugar chain represented by (Formula 1) below:

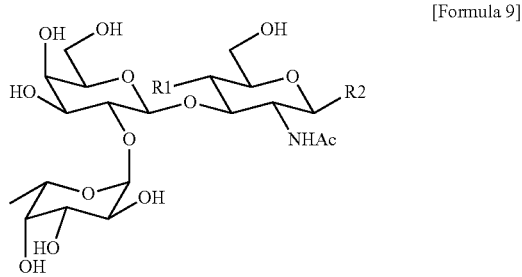

[Formula 9]

wherein R1 represents an OH group or any sugar chain and R2 represents an OH group or any sugar chain, protein, lipid, or another molecule,
or (Formula 2) below:

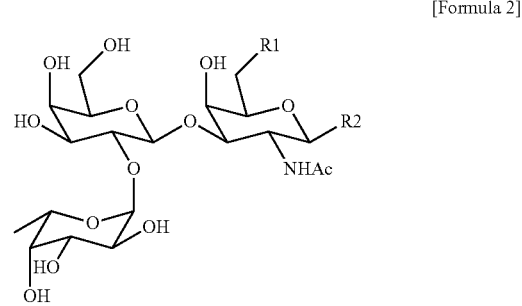

[Formula 2]

wherein R1 represents an OH group or any sugar chain and R2 represents an OH group or any sugar chain, protein, lipid, or another molecule, contained in a culture supernatant or a lysate of cells.

Specifically, the stem cell is detected by steps of: contacting the culture supernatant or the lysate, a lectin capable of binding to the sugar chain, and an antibody capable of binding to keratan sulfate to form a complex comprising the lectin, the sugar chain, and the antibody; and detecting the complex.

Sugar chain structures represented by the (Formula 1) and (Formula 2) have been demonstrated to be specifically present on the cell surface, and in the culture supernatant, of an undifferentiated cell and be derived from podocalyxin (see Patent Literatures 1 and 2). Thus, the method for detecting a stem cell according to the present invention is more specifically a method for detecting a stem cell by detecting podocalyxin contained in a culture supernatant or a lysate of cells, the method comprising steps of: contacting the culture supernatant or the lysate, a lectin capable of binding to a sugar chain represented by the (Formula 1) or (Formula 2), and an antibody capable of binding to keratan sulfate to form a complex composed of the lectin, podocalyxin, and the antibody; and detecting the complex.

[Sugar Chain Structure]

The (Formula 1) represents the sugar chain structure of "Fucα1-2Galβ1-3GlcNAc". The hydroxyl group at position 4 of GlcNAc may be substituted by a monosaccharide (preferably, fucose) or a branched or unbranched oligosaccharide chain (preferably, a sugar chain consisting of 2 to 5 sugars). The sugar chain structure is a sugar chain binding to the nonreducing end of a glycoprotein, a glycolipid, a saccharide, or the like at position 1 of GlcNAc as a membrane constituent on the stem cell surface; and thus the OH group or the nonreducing end of another saccharide, protein, lipid, or the another molecule may bind to position 1 of GlcNAc.

The (Formula 2) represents the sugar chain structure of "Fucα1-2Galβ1-3GalNAc". The hydroxyl group at position 1 of GalNAc may be substituted by a monosaccharide (preferably, fucose) or a branched or unbranched oligosaccharide chain (preferably, a sugar chain consisting of 2 to 5 sugars). The sugar chain structure is a sugar chain binding to the nonreducing end of a glycoprotein, a glycolipid, a saccharide, or the like at position 1 of GalNAc as a membrane constituent on the stem cell surface; and thus the OH group or the nonreducing end of another saccharide, protein, lipid, or the another molecule may bind to position 1 of GalNAc.

[Lectin]

BC2LCN lectin or its modified product is preferably used as a lectin capable of binding to a sugar chain represented by the (Formula 1) or (Formula 2). The amino acid sequence of BC2LCN lectin is of SEQ ID NO: 1. In addition to a protein comprising the amino acid sequence of SEQ ID NO: 1, a protein comprising an amino acid sequence in which 1 or several amino acids are deleted, substituted, inserted, or added in the amino acid sequence and being capable of binding to a sugar chain represented by the (Formula 1) or (Formula 2) (a modified product of BC2LCN lectin) is also preferably used as the lectin. In addition to these lectins, a lectin recognizing a sugar chain represented by the (Formula 1) and/or Formula 2) can be further used without particular limitation.

BC2LCN lectin is an N-terminal domain of BC2L-C protein derived from a gram-negative bacterium (*Burkholderia cenocepacia*) (see Non Patent Literature 2). A recombinant protein obtained by expressing the BC2LCN lectin in *Escherichia coli* (rBC2LCN lectin) can be preferably used as the lectin capable of binding to a sugar chain represented by the (Formula 1) or (Formula 2). rBC2LCN lectin can be produced on a large scale using transformed bacteria. Specifically, BC2LCN gene encoding the amino acid sequence of SEQ ID NO: 1 is incorporated into an expression vector and introduced and expressed in a host cell, followed by purifying the protein, if necessary, to prepare rBC2LCN lectin.

BC2LCN lectin and rBC2LCN lectin and their modified products are not required to contain the full length of the amino acid sequence of SEQ ID NO: 1 provided that they can bind to a sugar chain represented by the (Formula 1) or (Formula 2), and 1 or several amino acids may be deleted, substituted, inserted, or added in SEQ ID NO: 1. Here, "several" represents a natural number of 20 or less, preferably 10 or less, more preferably 5 or less.

[Antibody]

An IgG antibody produced by hybridoma R-10G (accession number: FERM BP-11301) is preferably used as the antibody capable of binding to keratan sulfate. The antibody produced by hybridoma R-10G (hereinafter also referred to as "R-10G antibody") is described in Patent Literature 3. R-10G antibody is a monoclonal antibody obtained by screening hybridomas prepared using a human iPS cell as an immunogen by use of human iPS cell positivity and human embryonal carcinoma cell negativity as an index. It has been demonstrated that the epitope for R-10G antibody is keratan sulfate having a low degree of sulfation (the antibody does not react with keratan sulfate having a high degree of sulfation) and the polypeptide portion of the epitope is podocalyxin (see Non Patent Literature 3). According to Non Patent Literature 3, the epitope for R-10G antibody is considered to contain "Gal-GlcNAc (6S)" or its tandem repeat. R-10G antibody can be prepared according to the method described in Patent Literature 3; however, the antibody may be a commercially available one (for example, RIT-M001, Cosmo Bio Co., Ltd.).

Keratan sulfate contains a repeated structure of "Gal-GlcNAc (6S)", and Gal in "Gal-GlcNAc (6S)" provides a sulfation site. The degree of sulfation means the degree of sulfation of this Gal.

In addition to R-10G antibody, an antibody competing with the antibody can also be used as the antibody capable of binding to keratan sulfate. The antibody competing with R-10G antibody means an antibody competing with R-10G antibody in binding to keratan sulfate, that is, an antibody capable of binding to the epitope bound by R-10G antibody. The antibody competing with R-10G antibody can be obtained by determining the competition of a candidate antibody for the binding of R-10G antibody to podocalyxin (that is, a candidate antibody prevents the binding of R-10G antibody to podocalyxin) using a heretofore known competitive binding assay. The competitive binding assay enables a competitive antibody to be obtained even when the specific epitope for R-10G antibody has not been determined; however, the competitive antibody is preferably an antibody which uses low-sulfated keratan sulfate as an epitope and, particularly, for which the epitope contains Gal-GlcNAc (6S) or its tandem repeat.

In addition, as the antibody capable of binding to keratan sulfate, an antibody recognizing keratan sulfate, preferably low-sulfated keratan sulfate, can be used without particular limitation, in addition to an R-10G antibody and an antibody competing with the antibody.

For the purpose of the present invention, the term "antibody" here also includes "a functional fragment of an antibody". The "functional fragment of an antibody" means a partial fragment of an antibody, having an activity of binding to an antigen, and includes, for example, Fab, F(ab')2, and scFv. The functional fragment of an antibody also includes Fab' as a monovalent fragment of the variable region of an antibody obtained by treating F(ab')2 under reduced conditions. However, the fragment is not limited to these molecules provided that it has the ability to bind to an antigen. The functional fragment includes not only one obtained by treating the full-length molecule of an antibody protein with a suitable enzyme but also a protein produced in a suitable host cell using an antibody gene modified by a genetic engineering technique.

[Stem Cell]

The "stem cell" is generally defined as an undifferentiated cell having "self-renewal ability" enabling proliferation while retaining an undifferentiated state and "pluripotent differentiation ability" enabling differentiation into all triploblastic lineages. The stem cell (multipotential stem cell) which the detection method according to the present invention is to detect is an undifferentiated cell having self-renewal ability and pluripotent differentiation ability and at least includes a pluripotent stem cell and a multipotent stem cell. Examples of the stem cell include in particular an embryonic stem cell (ES cell), and an induced pluripotent cell (iPS cell) obtained by introducing reprogramming factors into a somatic cell. The multipotent stem cell includes somatic stem cells, such as a mesenchymal stem cell, a hematopoietic stem cell, a neural stem cell, a myeloid stem cell, and a germ stem cell. According to the present invention, the simply described "cell" is intended to be used in the sense of including both a stem cell and a differentiated cell (somatic cell).

The species from which the cell is derived is not particularly limited, and may be, for example, a human, a monkey, a pig, cattle, a goat, sheep, a mouse, or a rat.

[Culture Supernatant/Lysate]

The sugar chain structure represented by (Formula 1) and/or (Formula 2) has been shown to specifically present on the cell surface of an undifferentiated cell and in the culture supernatant thereof (see Patent Literatures 1 and 2); thus, in the method for detecting a stem cell according to the present invention, the sample used for detecting the stem cell may be a lysate of cells or a culture supernatant thereof.

The culture supernatant and lysate of cells can be prepared according to heretofore known methods. The lysate can be prepared by a method involving physically crushing cells or a method involving chemically solubilizing cells. A method involving solubilizing cells using a surfactant is preferable in view of causing no thermal denaturation of protein, deactivating no protein, making the protein recovery rate favorable, simplifying operation, and the like.

For example, a cytolytic agent containing a surfactant is added to a pellet of $5 \times 10^6$ to $5 \times 10^7$ cells to suspend the cells, followed by reaction on ice for 1 to 10 minutes. Then, centrifugation is carried out at 20,000×g for about 15 minutes, and the resultant supernatant may be used as a cell lysate.

As the cytolytic agent, a buffer solution containing suitable salts (e.g., KCl and NaCl) and a reducing agent, such as DTT, to which a surfactant as a cytolytic agent conventionally used in the art is added is used. The buffer solution is preferably, for example, a phosphate buffer solution, a TRIS buffer solution, a Good's buffer solution, a glycine buffer solution, or a borate buffer solution, which has a buffer action around a neutrality of pH 5.0 to 10.0, preferably pH 7.0 to 8.0. The concentration of a buffering agent in the buffer solution is properly selected typically from the range of 10 to 500 mM, preferably 10 to 100 mM. The salt concentration is typically 100 to 200 mM. The surfactant may be properly selected according to conditions, such as the type of the cell, the pH and salt concentration of the buffer solution used. Examples thereof include NP-40, poly(oxyethylene)nonylphenyl ether (Wako Pure Chemical Industries Ltd.), TritonX-100, and digitonin. The concentration thereof is considered to be typically on the order of 0.01 to 1.0% based on the total amount of the buffer solution.

The culture supernatant and the lysate may contain serum. According to the method for detecting a stem cell according to the present invention, the presence of the stem cell can be detected with high sensitivity even when the culture supernatant and lysate of cells cultured in a serum-containing medium is used (see Test Example 1).

As the medium, a medium conventionally used for the maintenance of undifferentiation and differentiation induction of stem cells may be used. For example, there can be used StemSure® hPSC medium (Wako Pure Chemical Industries Ltd.), Nutristem® (Biological Industries Ltd.), ReproFF (ReproCELL), TeSR™-E8™ (STEMCELL Technologies), Essential 8™ Medium (LifeTechnologies), StemPro® hESC SFM (LifeTechnologies), and mTeSR1 (STEMCELL Technologies).

The serum is not particularly limited, and there is used, for example, calf serum (CS), fetal bovine serum (FBS), human-derived serum, bovine-derived serum, sheep-derived serum, goat-derived serum, monkey-derived serum, horse-derived serum, rat-derived serum, mouse-derived serum, rabbit-derived serum, hamster-derived serum, guinea pig-derived serum, porcine-derived serum, bird (avian)-derived serum, dog-derived serum, or cat-derived serum. The concentration of the serum in the culture supernatant and the lysate can vary depending on the concentration thereof added to the medium. The concentration of the serum added to the medium for the conventional maintenance culture or differentiation culture of stem cells is on the order of 0.5 to 20% (v/v).

The culture supernatant and the lysate can be used directly or by dilution without passing through a purification step, or by concentration with an antibody, a lectin, or the like in advance.

The method for detecting a stem cell according to the present invention is highly sensitive and thus can detect a pico-molar (pM) or nano-molar (nM) level of a sugar chain represented by the (Formula 1) or (Formula 2) in an amount of on the order of 0.1 to 10 µl in the culture supernatant.

[Lectin-Antibody Sandwich Method]

Steps of the method for detecting a stem cell according to the present invention include a complex formation step of contacting the culture supernatant or the lysate (hereinafter also referred to as "culture supernatant or the like"), a lectin, and an antibody capable of binding to keratan sulfate to form a complex composed of the lectin, podocalyxin, and the antibody and a detection step of detecting the complex. These steps will be specifically described below taking for example a case where rBC2LCN lectin and R-10G antibody are used.

In the complex formation step, rBC2LCN lectin and R-10G antibody may be simultaneously contacted with the culture supernatant or the like; however, more preferably, the culture supernatant or the like is contacted with rBC2LCN lectin and then reacted with R-10G antibody. Specifically, the complex formation step preferably consists of a first step of contacting the culture supernatant or the like with the lectin to form a first complex composed of rBC2LCN lectin and podocalyxin contained in the culture supernatant or the like, and a second step of contacting the first complex with R-10G antibody to form a second complex composed of rBC2LCN lectin, podocalyxin, and R-10G antibody.

The complex formation step may be carried out using a homogenous method in which B/F separation is not performed; however, it is more preferably carried out using a heterogeneous method in which B/F separation is performed using an insoluble support.

The amount of the culture supernatant or the like and the amounts (concentrations) of the lectin and the antibody for reacting therewith are properly set depending on the type of the cell, the measurement sensitivity required, the measurement method and measuring device used, and the like.

The method involving B/F separation using an insoluble support is carried out, for example, by contacting rBC2LCN lectin bound to the insoluble support, R-10G antibody not bound to the insoluble support, and the culture supernatant or the like to form a complex. More specifically, the method involving B/F separation is carried out by a first step of contacting the culture supernatant or the like with rBC2LCN lectin bound to the insoluble support to provide a first complex composed of rBC2LCN lectin and podocalyxin, and a second step of contacting the first complex with free R-10G antibody to provide a second complex composed of rBC2LCN lectin, podocalyxin, and R-10G antibody.

The insoluble support for B/F separation can use a base material used for a conventional protein immobilization method, such as a glass slide, an ELISA plate (microplate), a magnetic bead, a filter, a film, or a membrane. As a material for the base material, glass, silicon, polycarbonate, polystyrene, polyurethane, or the like is typically used.

The method for immobilizing the lectin on the insoluble support is not particularly limited, and a well-known method, such as a chemical binding method (a method involving immobilization by covalent binding) and a physical adsorption method. It is also possible to immobilize the lectin on the insoluble support using an extremely strong binding reaction such as avidin-biotin reaction. In this case, a biotinylated lectin in which biotin is bound to the lectin may be immobilized on a streptavidin plate in which streptavidin is coated thereon. The lectin may also be immobilized on the insoluble support through any of various linkers conventionally used in the art.

The method involving B/F separation using an insoluble support may comprise a washing step for removing unnecessary substances from the solid phase surface before performing the second step of reacting the first complex with the free R-10G antibody after the first step of reacting the culture supernatant or the like with rBC2LCN lectin immobilized on the insoluble support. The method may also comprise the washing step before performing the detection step after the second step. The washing step can remove contaminants in the sample and unreacted R-10G antibody from the solid phase surface to separate only the second complex on the solid phase surface.

In the method not involving B/F separation, as a method for separating the complex of rBC2LCN lectin, podocalyxin, and R-10G antibody, for example, a chromatographic method, a high-performance liquid chromatographic method, an electrophoretic method, a capillary electrophoretic method, a capillary chip electrophoretic method, or a method using an automated immunology analyzer, such as LiBASys (from Shimadzu Corporation) can be applied.

The detection step can be carried out by detecting the second complex composed of rBC2LCN lectin, podocalyxin, and R-10G antibody using a marker. Examples of the marker include markers used in a conventional immunoassay method or the like, including enzymes, radioisotopes, fluorescent substances, luminescent substances, DNA, RNA, coenzymes or substances (biotin, avidin) specifically binding to coenzymes, tags, substances having absorption in the ultraviolet to infrared region, chromogenic fine particles, metallic fine particles, fluorescent fine particles, magnetic substances, and substances having a property as spin labeling agents.

The binding of a marker to rBC2LCN lectin and/or R-10G antibody, preferably R-10G antibody may be carried out, for example, properly using a labeling method performed in a conventional immunoassay method or the like. A method can also be adopted which involves binding a marker to the antibody through 1 or several amino acids or through 1 or several amino acids and a linker. In addition, since various kits for binding markers to proteins are commercially available, the kits may each be used to perform labeling according to the instruction manual included therewith.

For example, the method involving B/F separation using rBC2LCN lectin immobilized on an insoluble support and free R-10G antibody labeled with horseradish peroxidase (HRP) as a marker is roughly as follows.

The culture supernatant or the like is contacted with an insoluble support on which rBC2LCN lectin is immobilized to conduct reaction at 4 to 40° C. for 3 minutes to 20 hours to produce a first complex of rBC2LCN lectin and podocalyxin on the solid phase surface. Then, a solution containing R-10G antibody labeled with HRP is added onto the solid phase surface, which is then reacted at 4 to 40° C. for 3 minutes to 16 hours to produce a second complex of immobilized rBC2LCN lectin-podocalyxin-labeled R-10G antibody. Subsequently, a suitable concentration of a TMB (3,3',5,5'-tetramethylbenzidine) solution is added thereto, which is reacted for a certain time. Then, a reaction termination solution, such as 1 M sulfuric acid, is added to stop the reaction, and absorbance is measured at 450 nm. The amount of podocalyxin (or, a sugar chain represented by the (Formula 1) or (Formula 2) on podocalyxin) in the culture supernatant or the like can be determined from the resultant measured value and a calibration curve obtained by performing the same measurement for podocalyxin solutions with known concentrations in advance.

The sugar chain represented by the (Formula 1) or (Formula 2) can also be measured according to the well-known fluorescence correlation spectroscopy (FCCS) using rBC2LCN lectin labeled, for example, with Alexa Fluor-488 tetrafluorophenyl ester and R-10G antibody labeled, for example, with Alexa Fluor-647 succinimidyl ester.

The complex of "rBC2LCN lectin-podocalyxin-R-10G antibody" can also be detected, for example, by a measurement method using a property originating from the complex, specifically a method, such as a homogeneous immunoassay system (e.g., surface plasmon resonance), without using a marker.

The lectin-antibody sandwich method according to the present invention is not limited to a hand method and can also be applied to a measurement system using an automated analyzer for easy and rapid measurement. The combination of reagents or the like when measurement is performed using a hand method or an automated analyzer is not particularly limited; in accordance with the environment and model of the automated analyzer applied or taking into consideration other factors, a combination of reagents or the like deemed best may be selected and used. In addition, the lectin-antibody sandwich method according to the present invention can also be applied to Micro-TAS (Micro-Total Analysis Systems: μ-TAS, μ comprehensive analysis system).

[Application]

Since sugar chain structures represented by the (Formula 1) and (Formula 2) are specifically present on the cell surface, and in the culture supernatant, of an undifferentiated cell, the detection method according to the present invention can detect the sugar chains on podocalyxin contained in the culture supernatant or the like of cells to detect the presence of a stem cell present among the cells. The quantitative detection of the sugar chain also enables the determination of the abundance of stem cells among cells.

For example, a given amount of the culture supernatant or the like of stem cells cultured to maintain an undifferentiated state (subjected to maintenance culture) is collected using a micropipette or the like to detect a sugar chain represented by the (Formula 1) and/or (Formula 2) on podocalyxin by the detection method according to the present invention. The detection of the sugar chain can confirm the maintenance of the undifferentiated state of the cells, enabling high quality stem cells to be obtained without contaminated differentiated cells. Alternatively, based on the quantitative value of the sugar chain, it can also be determined how much proportion of cells in total cells maintains an undifferentiated state (conversely, how much proportion is differentiated).

The means for collecting a given amount of the culture supernatant or the like may be handwork but can also be automatic collection using an automatic culture apparatus or the like.

In addition, for example, after inducing the differentiation of stem cells, a given amount of the culture supernatant or the like of cells is collected using a micropipette or the like to detect a sugar chain represented by the (Formula 1) and/or (Formula 2) on podocalyxin by the detection method according to the present invention. The detection of the sugar chain can confirm the remaining of stem cells in an undifferentiated state among the cells. Conversely, the differentiation of all cells can be confirmed if the sugar chain is no longer detected (its level reaches the same as the background value), enabling differentiated cells at no risk of contamination with undifferentiated cells to be obtained. Alternatively, based on the quantitative value of the sugar chain, it can also be determined how much proportion of cells in total cells are differentiated (conversely, how much proportion of cells remains in an undifferentiated state).

When the culture supernatant of cells is provided for the detection method according to the present invention, it is necessary to use the culture supernatant after a sugar chain of the (Formula 1) or (Formula 2) is secreted in a detectable amount. After replacement, the time it takes for the appearance of a detectable amount of the sugar chain in the culture solution can vary and be properly set depending on the type and culture conditions of the cells; however, it is considered to be, for example, on the order of 18 to 30 hours. The medium is typically replaced every about 24 hours; thus, it is preferable to use a portion of the culture supernatant discarded at the time.

Here, the method for inducing the differentiation of stem cells may be any method. For example, methods can be applied, including a method involving culturing stem cells in the presence of retinoic acid for differentiation into neural cells and a method for forming epidermal cells using the surface of NIH3T3 cells whose proliferation have been stopped as a platform.

2. Kit for Detecting Stem Cell

The kit for detecting a stem cell according to the present invention is one used for the method for detecting a stem cell, and comprises a lectin capable of binding to a sugar chain represented by (Formula 1) below:

[Formula 11]

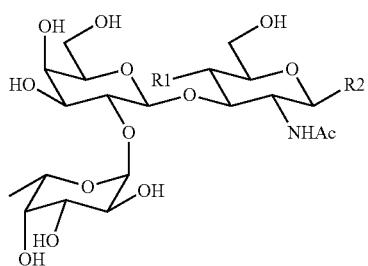

wherein R1 represents an OH group or any sugar chain and R2 represents an OH group or any sugar chain, protein, lipid, or another molecule,
or (Formula 2) below:

[Formula 12]

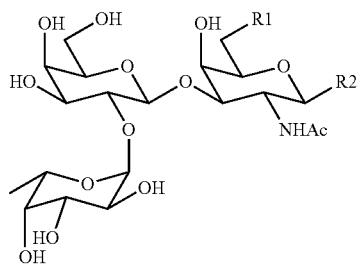

wherein R1 represents an OH group or any sugar chain and R2 represents an OH group or any sugar chain, protein, lipid, or another molecule, and an antibody capable of binding to keratan sulfate.

A preferable aspect and specific examples of the composition of the kit are as described in the method for detecting a stem cell. Specifically, the antibody capable of binding to keratan sulfate is preferably an antibody capable of binding, particularly to low-sulfated keratan sulfate. The epitope for the antibody also preferably comprises Gal-GlcNAc (6S) or a tandem repeat thereof. Specifically, an antibody produced by hybridoma R-10G (accession number: FERM BP-11301) or an antibody competing with the antibody can be used.

Reagents included in the kit may include reagents conventionally used in the art, for example, a buffering agent, a reaction accelerator, saccharides, a protein, salts, a stabilizer (e.g., surfactant), and a preservative, which neither inhibit the stability of coexisting reagents and the like nor inhibit the reaction of podocalyxin with the lectin and the antibody. The concentrations thereof may also be properly selected from the concentration ranges conventionally used in the art. In addition, the kit may include a standard used for preparing a calibration curve for podocalyxin.

According to the kit for detecting a stem cell in accordance with the present invention, the lectin capable of binding to a sugar chain represented by the (Formula 1) or (Formula 2) is preferably bound to an insoluble support. The antibody capable of binding to keratan sulfate is preferably labeled in advance; however, a reagent for users to label the antibody before using may be included in the kit.

The terms and concepts according to the present invention are based on the meanings of the terms idiomatically used in the art, and various techniques used for practicing the present invention can be easily and positively performed by one of ordinary skill in the art based on known literature and the like, particularly except for the techniques whose written sources are acknowledged.

Various analyses and the like have been performed in line with methods as described in the instruction manuals, catalogs, or the like of the analyzers, reagents, or kits used.

Reference shall be made as the contents of description of the present invention to the contents described in the art references, patent publications, and patent application specifications cited herein.

EXAMPLES

Test Example 1: Detection of Stem Cell by Lectin-Antibody Sandwich Method

To evaluate the method for detecting stem cells by the lectin-antibody sandwich method according to the present invention, podocalyxin was quantitatively measured using dilutions of the culture supernatant of iPS cells. Measurement was performed by the ELISA detection system using a microplate.

Biotinylated rBC2LCN lectin (0.5 μg equivalent) was added to each well of a streptavidin plate (Sumitomo Bakelite Co., Ltd.) and immobilized at 37° for 1 hour. The preparation of a recombinant lectin was according to the method described in Non Patent Literature 4. After washing the well with a buffer solution (1% TritonX-100, phosphate buffer solution), 50 μl each of solutions obtained by serially diluting the culture supernatant of iPS cells (strain 201B7) cultured in mTeSR1 medium for 24 hours with a medium (2% FBS, DMEM) were each added to the well and reacted at 37° C. for 1 hour. The iPS cells (strain 201B7) were obtained from Riken BioResource Center.

After washing the well with the buffer solution, R10G antibody labeled with peroxidase (0.1 μg/ml) was added to the well and reacted at 37° C. for 1 hour. After washing the well with the buffer solution, 100 μl of a substrate solution (TMB, Wako Pure Chemical Industries Ltd.) was added to the well and reacted at room temperature for 30 minutes. The reaction was stopped by adding 1 M sulfuric acid, followed by measuring absorbance (450 nm) in each well. For comparison, rABA lectin (derived from *Agaricus bisporus*, see Patent Literature 2), an anti-SSEA3 antibody, an anti-SSEA4 antibody, an anti-Tra-1-60 antibody, an anti-Tra-1-81 antibody, or an anti-podocalyxin antibody was used at the same concentration in place of R10G antibody.

(1) R10G antibody: Low-sulfated keratin antibody (Cosmo Bio Co., Ltd., RIT-M001). It recognizes keratan sulfate having a low degree of sulfation (low-sulfated keratan sulfate) on podocalyxin.
(2) rABA lectin: Its amino acid sequence is of SEQ ID NO: 2 (also see RCSB Protein Data Bank Accession No. 1Y2V).
(3) Anti-SSEA3 antibody: Rat monoclonal IgM antibody (Millipore, MAB4303). It recognizes SSEA3 antigen (stage-specific embryonic antigen 3) expressed on the surface of a human EC cell (tetracarcinoma stem cell), a human EG cell (embryonic germ cell), and a human ES cell.
(4) Anti-SSEA4 antibody: Mouse monoclonal IgG antibody (Millipore, MAB4304). It recognizes SSEA4 antigen (stage-specific embryonic antigen 4) expressed on the surface of a human EC cell, a human EG cell, and a human ES cell.

(5) Anti-Tra-1-60 antibody: Mouse monoclonal IgM antibody (Millipore, MAB4360). It recognizes keratan sulfate on podocalyxin (see Non Patent Literatures 5 and 6).
(6) Anti-Tra-1-81 antibody: Mouse monoclonal IgM antibody (Millipore, MAB4381). It recognizes keratan sulfate on podocalyxin (see Non Patent Literatures 5 and 6).
(7) Anti-podocalyxin antibody: Goat polyclonal IgG antibody (R&D System. AF1658). It recognizes human podocalyxin.

Figure 2:
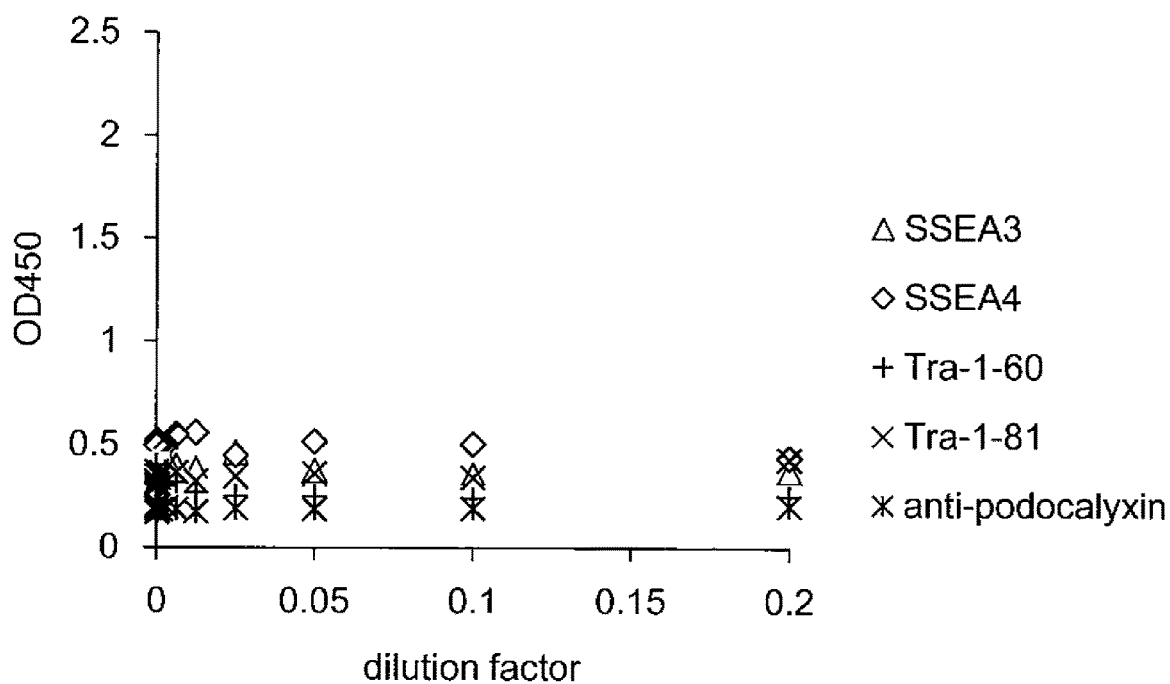
FIG. 2 is a graph showing the results of evaluating the method for detecting stem cells by the lectin-antibody sandwich method according to the present invention by comparison with those by lectin-antibody sandwich methods using various antibodies (Test Example 1).

The results are shown in FIGS. 1 and 2. In the case of using rABA lectin, the use of a dilution having a dilution fold as high as 40 times (in the figure, dilution factor: 0.025) or less resulted in a marked influence of background, and reduced quantitativity (the determination coefficient of a linear regression line: 0.6387). As the cause thereof, an increase in background due to the non-specific binding between the serum component in the medium and rBC2LCN lectin and rABA lectin was considered.

In the case of using R10G antibody, any dilution fold did not cause an increase in background due to the non-specific binding described above, enabling high-precision quantitative measurement (the determination coefficient of a linear regression line: 0.9988).

The anti-SSEA3 antibody and the anti-SSEA4 antibody lacked reactivity with the antigen, not enabling measurement (see FIG. 2). When the anti-Tra-1-60 antibody and the anti-Tra-1-81 antibody, recognizing keratan sulfate on podocalyxin, were used, they were also little or completely not bound to the antigen not enabling measurement (see FIG. 2). As the cause thereof, the following were considered.

Both the anti-Tra-1-60 antibody and the anti-Tra-1-81 antibody are antibodies using keratan sulfate on podocalyxin as an epitope; however, they are different in the epitope from R-10G antibody for which the epitope contains "Gal-Glc-NAc (6S)" or its tandem repeat since the epitope for the antibodies is considered to contain "Galβ1-3GlcNAcβ1-3Galβ1-4GlcNAc (6S)" (see Non Patent Literature 7).

The anti-Tra-1-60 antibody and the anti-Tra-1-81 antibody are considered to use high-sulfated keratan sulfate as an epitope, and are different in the epitope from R-10G antibody using low-sulfated keratan sulfate as an epitope.

Unlike R-10G antibody as an IgG antibody, the anti-Tra-1-60 antibody and the anti-Tra-1-81 antibody are IgM antibodies.

In addition, the use of the anti-podocalyxin antibody (R&D System. AF1658) also did not enable measurement. Possible causes thereof include that the antibody was not sufficiently reactive with podocalyxin expressed on stem cells since it was prepared using recombinant podocalyxin expressed in myeloma cells as an antigen. It is possible that the binding of the antibody to the epitope was inhibited by the specific structure of podocalyxin (for example, a sugar chain structure of (Formula 1) or (Formula 2)) resulting from expression on the stem cells.

Figure 3:
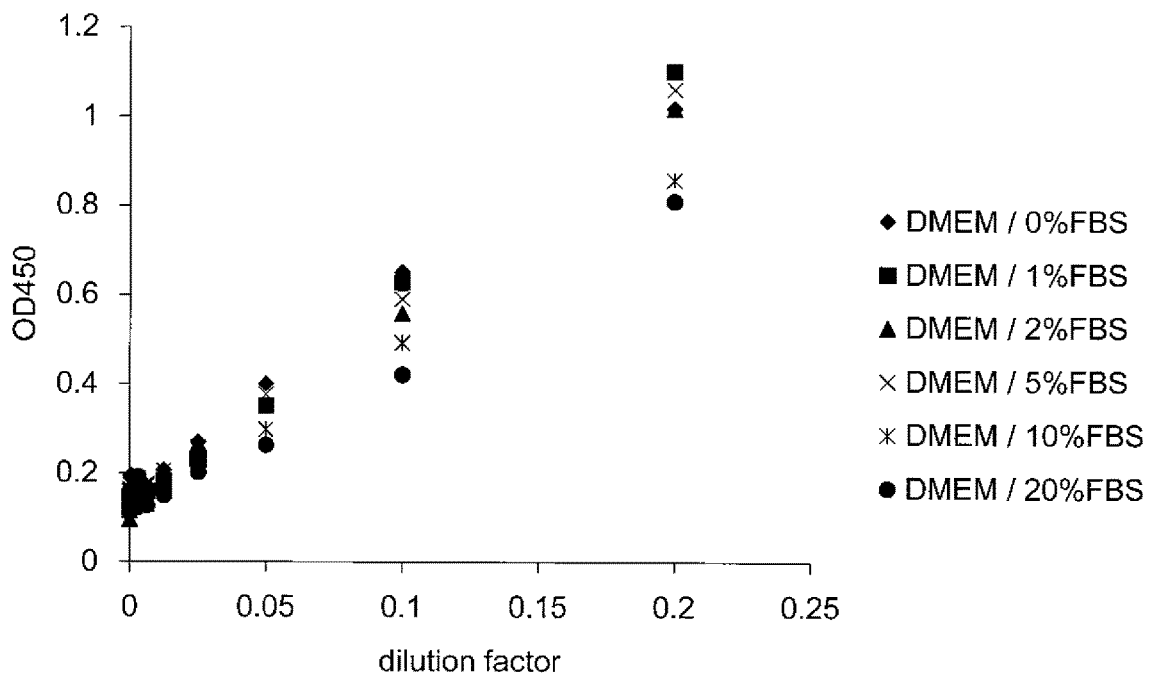
FIG. 3 is a graph showing the results of evaluating the method for detecting stem cells by the lectin-antibody sandwich method according to the present invention (Test Example 1).
Figure 4:
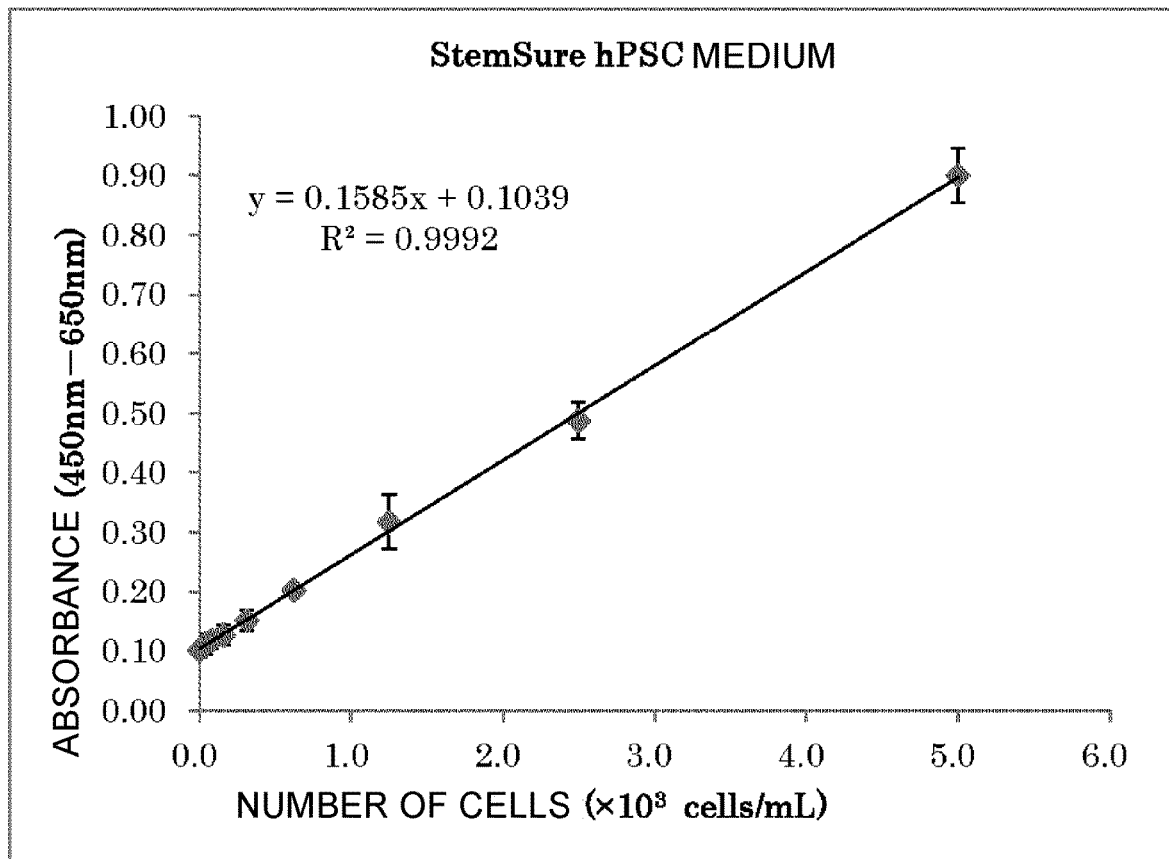
FIG. 4 is a graph showing the results of detecting stem cells cultured in a different type of medium (StemSure hPSC medium Δ) by the lectin-antibody sandwich method according to the present invention (Test Example 2).
Figure 5:
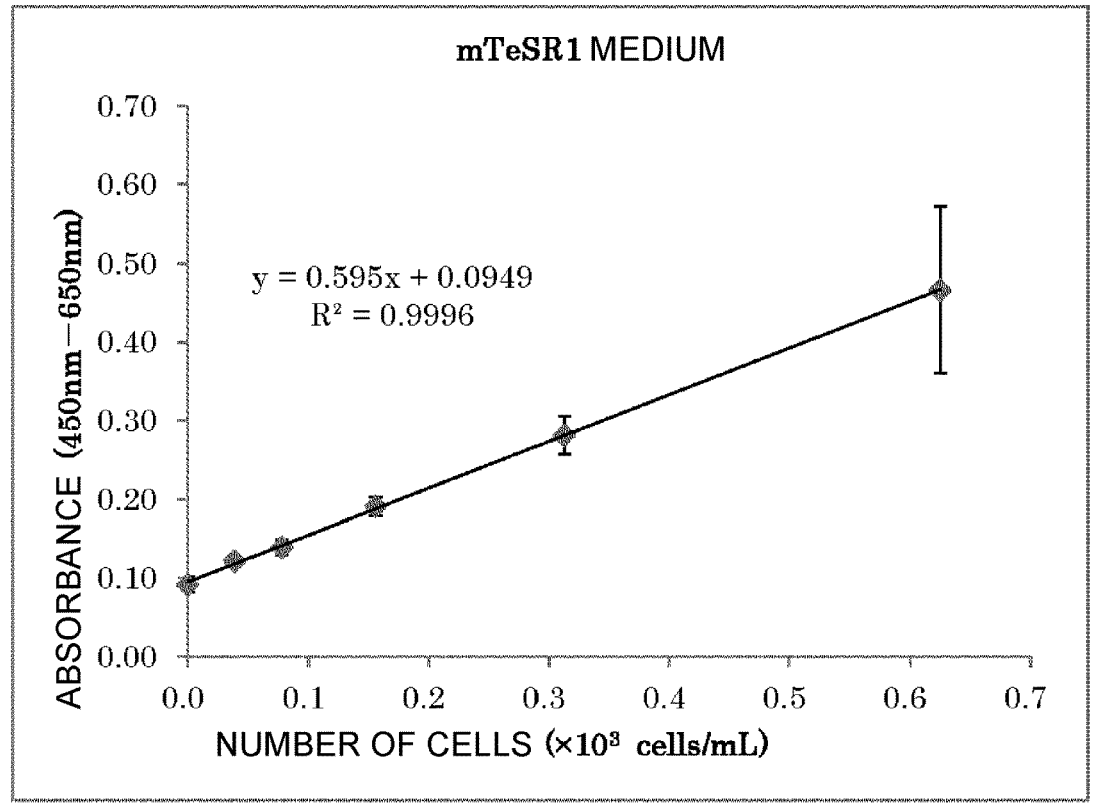
FIG. 5 is a graph showing the results of detecting stem cells cultured in a different type of medium (mTeSR1 medium) by the lectin-antibody sandwich method according to the present invention (Test Example 2).
Figure 6:
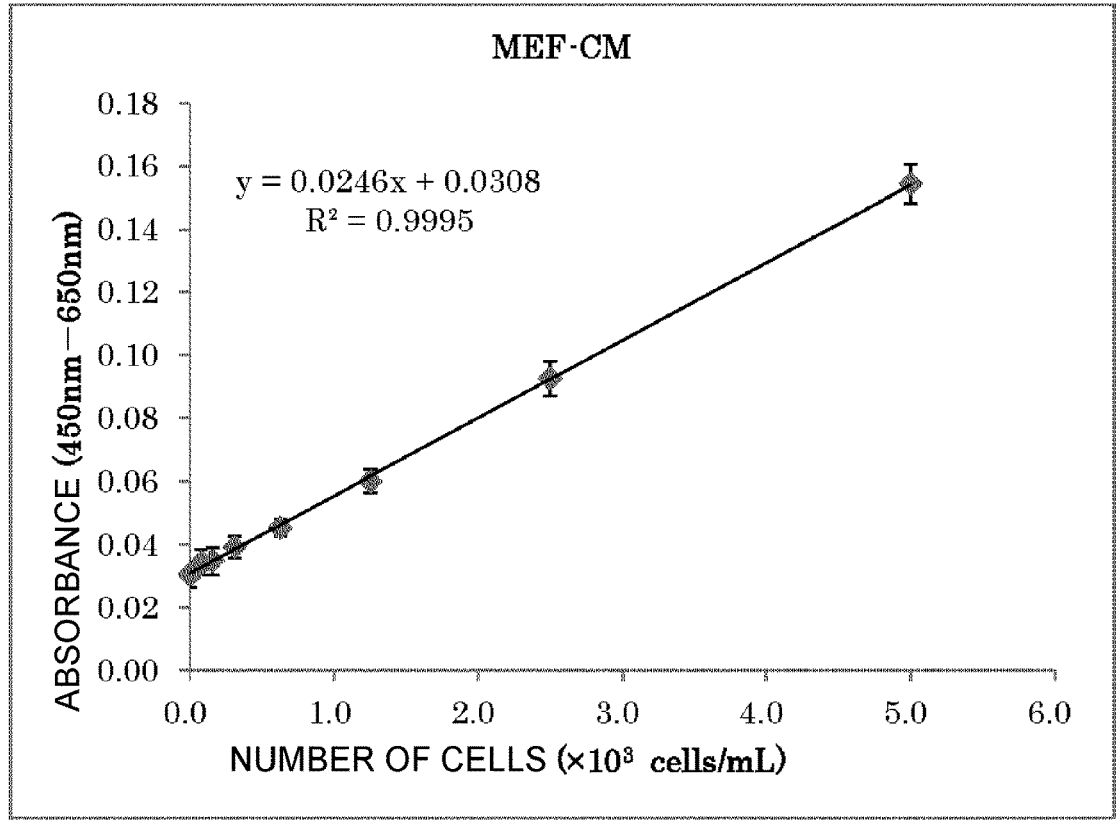
FIG. 6 is a graph showing the results of detecting stem cells cultured in a different type of medium (MEF-CM) by the lectin-antibody sandwich method according to the present invention (Test Example 2).
Figure 7:
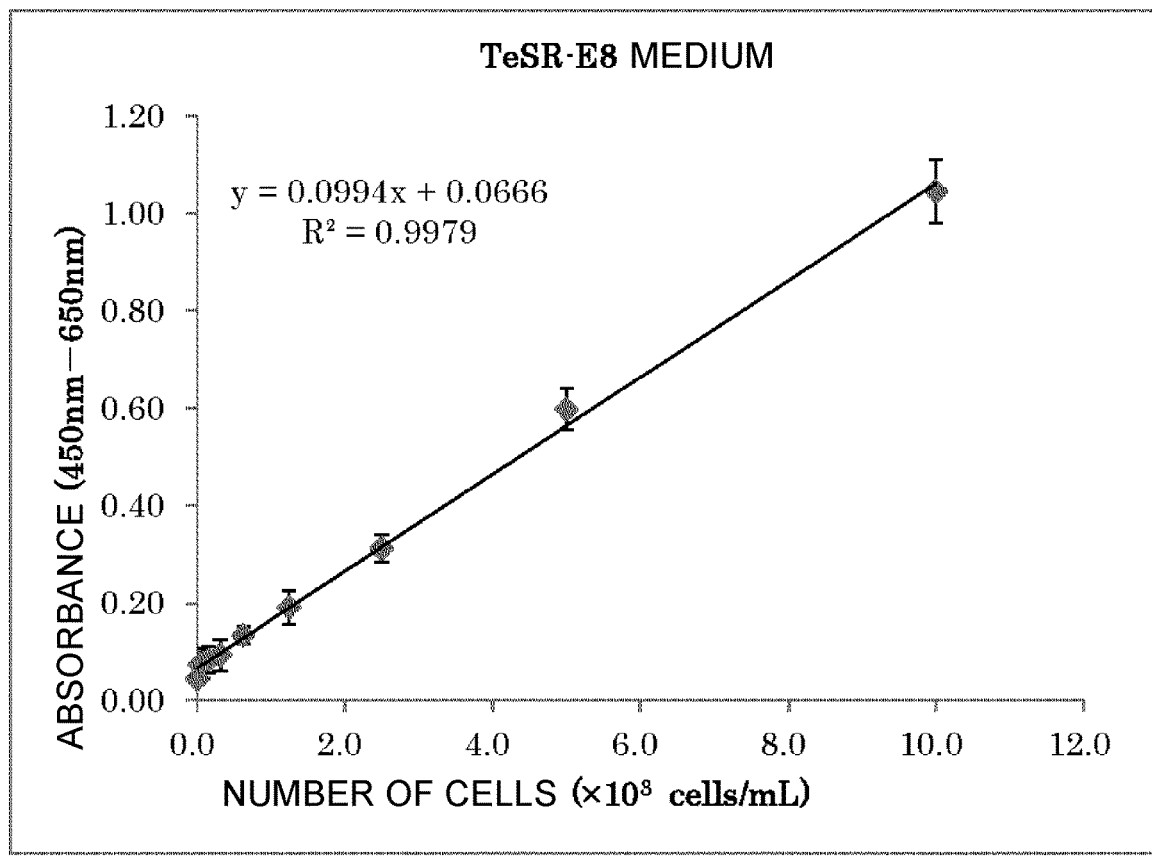
FIG. 7 is a graph showing the results of detecting stem cells cultured in a different type of medium (TeSR-E8 medium) by the lectin-antibody sandwich method according to the present invention (Test Example 2).

FIG. 3 shows the results of performing the quantitative measurement of podocalyxin using dilutions of the culture supernatant as described above except for changing the serum concentration in culturing iPS cells from 2% to 1%, 5%, 10%, or 20%. Good quantitativity could be confirmed in the serum concentration range of 1% to 20%.

Test Example 2: Calculation of Detection Limit Amount of Stem Cell by Lectin-Antibody Sandwich Method The quantitative measurement of podocalyxin was performed using dilutions of culture supernatants of iPS cells (strain 201B7) cultured in different types of media. The following 4 types of media were used as the media. After culturing iPS cells (strain 201B7) in each medium for 24 hours, the recovered culture supernatant was diluted with the medium to provide dilutions.

StemSure hPSC medium Δ (Wako Pure Chemical Industries Ltd.)
mTeSR1 medium (STEMCELL Technologies)
MEF-CM (mouse embryonic fibroblast-conditioned medium, the culture supernatant of cultured mouse embryonic fibroblasts)
TeSR-E8 medium (STEMCELL Technologies)

Biotinylated rBC2LCN lectin (0.3 µg/ml) was added to wells of a streptavidin plate and immobilized at room temperature (20° C. to 25° C.) for 1 hour. After washing the wells with a buffer solution (1% TritonX-100, phosphate buffer solution), 50 µl each of dilutions of each culture supernatant were added to the wells and reacted at room temperature for 1 hour.

After washing the wells with the buffer solution, R10G antibody labeled with peroxidase (0.5 µg/ml) was added to the wells and reacted at room temperature for 1 hour. After washing the wells with the buffer solution, 50 µl of a substrate solution (TMB) was added to the wells and reacted at room temperature for 30 minutes. After adding 0.5M sulfuric acid to the wells to stop the reaction, absorbance (450 nm to 650 nm) in each well was measured.

The results are shown in FIGS. 4 to 7. In the figure, the abscissa axis represents the dilution fold of the culture supernatant, and the dilution fold of the culture supernatant obtained under the culture condition of a cultured cell number per ml of medium of 10,000 is shown in a "number corresponding to cultured cells per ml of medium". Specifically, "10×10³ cells/ml" means no dilution; for example, "5.0×10³ cells/ml" means 2-fold dilution, "2.5×10³ cells/ml", 4-fold dilution, and "1.25×10³ cells/ml", 8-fold dilution. In the figure, the linear regression line and the regression equation are a line and an equation when the determination coefficient (R squared) is most favorable (near 1.0).

When any of the 4 types of media was used, good quantitativity was obtained even at a higher dilution fold. It could be determined that the lectin-antibody sandwich method according to the present invention was not affected by the type of the medium.

"Table 1" shows the results of determining a dilution fold providing a detection limit value based on the regression equation and calculating the detection limit value in the "number corresponding to cultured cells per ml of medium". The detection limit value was found by calculating the absorbance of the medium alone (a value obtained by adding 3.3 times the standard deviation to the average value of absorbance) and determining the dilution fold corresponding to the absorbance from the regression equation.

TABLE 1

| Medium | Detection Limit Number of Cells (cells/mL) |
| --- | --- |
| StemSure hPSC | 127 |
| mTeSR1 | 27 |
| MEF-CM | 321 |
| TeSR-E8 | 36 |

The "number corresponding to cultured cells per ml of medium" as a detection limit was 27 to 321 cells/ml. The detection limit for the "lectin-lectin sandwich method" in which rBC2LCN lectin and rABA lectin were combined according to the conventional art is reported to be 623 to 4,753 cells/ml (see Non Patent Literature 8). The "lectin-antibody sandwich method" in which rBC2LCN lectin and a low-sulfated keratin antibody, R10G antibody, were combined according to the present invention was demonstrated to be capable of detecting stem cells with much higher sensitivity than that of the conventional "lectin-lectin sandwich method".

Test Example 3: Detection of Stem Cell by Lectin-Antibody Sandwich Method—2

To evaluate the method for detecting stem cells by the lectin-antibody sandwich method according to the present invention, podocalyxin was quantitatively measured using dilutions of the culture supernatant of iPS cells. Measurement was performed by an array detection system using a glass slide.

Using a non-contact spotter (MicroSys4000; Genomic Solutions), rBC2LCN lectin was immobilized on an epoxy-activated glass slide. Each dilution of the culture supernatant prepared as in Test Example 1 was added dropwise onto a glass slide on which rBC2LCN lectin was immobilized, and reacted at 20° C. overnight. After washing, R10G antibody (1 μg/mL) was added dropwise thereto, which was then reacted at 20° C. for 1 hour. Then, a Cy3-labeled anti-mouse IgG antibody (JacksonImmunoResearch, 1 μg/mL) was added dropwise thereto, which was then reacted at 20° C. for 1 hour. After washing, the resultant was scanned using an evanescent wave excitation fluorescence scanner (Bio-REX Scan 200, Rexxam).

Figure 8:
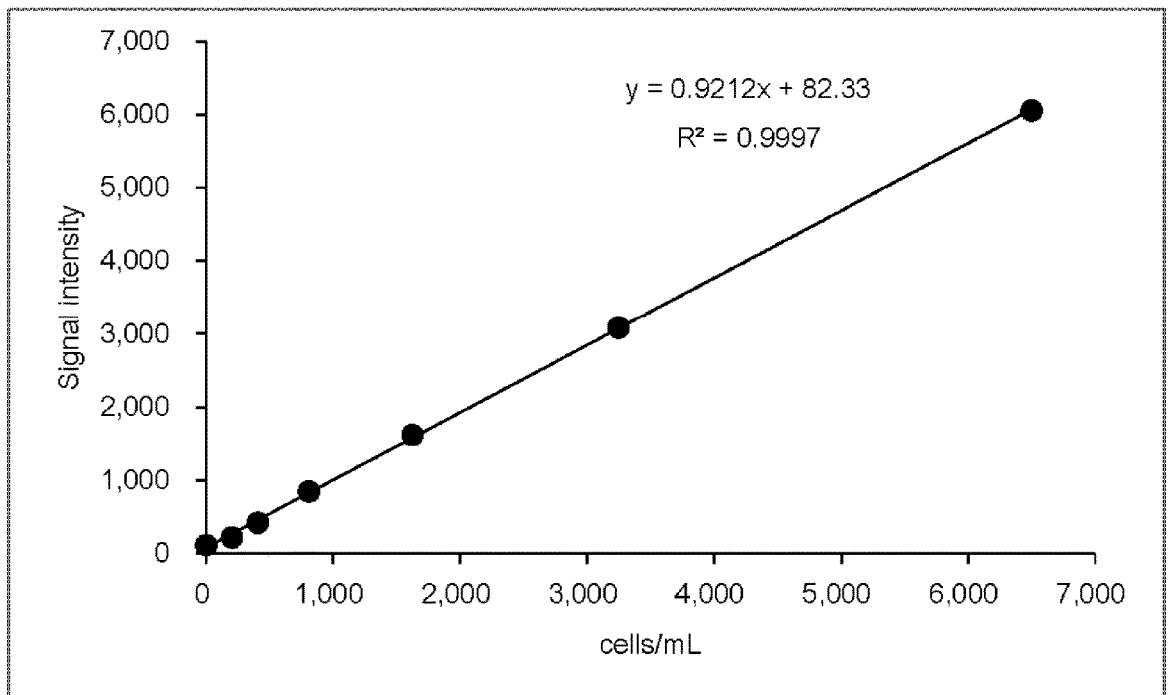
FIG. 8 is a graph showing the results of evaluating the method for detecting stem cells by the lectin-antibody sandwich method according to the present invention (Test Example 3).

The results are shown in FIG. 8. In the figure, the abscissa axis represents the dilution fold of the culture supernatant in a "number corresponding to cultured cells per ml of medium", as in FIGS. 1 to 4. In the figure, the linear regression line and the regression equation are a line and an equation when the determination coefficient (R squared) is most favorable (near 1.0).

No background due to non-specific binding was observed for any dilution fold, enabling high-precision quantitative measurement (the determination coefficient of a linear regression line: 0.9997).

The results of Test Examples 1 to 3 demonstrated that the lectin-antibody sandwich method in which rBC2LCN lectin was combined with a low-sulfated keratan sulfate antibody, R10G antibody, can detect podocalyxin with high precision even when the culture supernatant of cells cultured in a serum-containing medium was used, enabling the highly sensitive detection of stem cells. The same test using a water-soluble fraction obtained using a commercial kit (Cel-Lytic MEM Protein Extraction Kit, Sigma-Aldrich) from iPS cells (strain 201B7) cultured in mTeSR1 medium for 24 hours provided the same results as those from the test using the culture supernatant.

Sequence Listing Free Text

SEQ ID NO: 1: Amino acid sequence of rBC2LCN lectin

SEQ ID NO: 2: Amino acid sequence of ABA lectin

The material in the ASCII text file, named "PSK-9028US Seq.txt", created Aug. 2, 2017, file size of 4,096 bytes, is hereby incorporated by reference.

The invention claimed is:

1. A method for detecting a stem cell by detecting podocalyxin contained in a culture supernatant or a lysate of cells, the method comprising steps of:
   contacting the culture supernatant or the lysate,
      a lectin capable of binding to a sugar chain represented by (Formula 1) below:

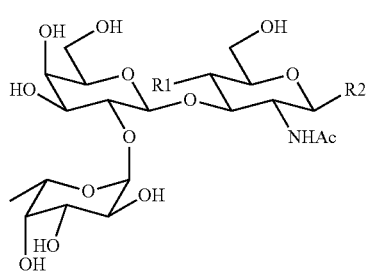

[Formula 1]

wherein R1 represents an OH group or any sugar chain and R2 represents an OH group or any sugar chain, protein, lipid, or another molecule,
   or (Formula 2) below:

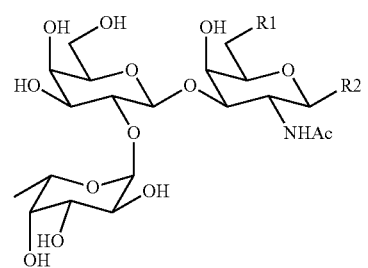

[Formula 2]

wherein R1 represents an OH group or any sugar chain and R2 represents an OH group or any sugar chain, protein, lipid, or another molecule, wherein the lectin is:
      a protein comprising the amino acid sequence of SEQ ID NO: 1 or
      a protein comprising an amino acid sequence in which one amino acid is deleted, substituted, inserted, or added in the amino acid sequence of SEQ ID NO: 1 and being capable of binding to a sugar chain represented by the (Formula 1) or (Formula 2), and
      an antibody capable of binding to keratan sulfate, wherein the antibody is an antibody produced by hybridoma R-10G (accession number: FERM BP-11301),
      to form a complex composed of the lectin, podocalyxin, and the antibody; and
   detecting the complex, wherein the detection of the complex is indicative of the presence of the stem cell.

2. The method according to claim 1, wherein the antibody is an antibody capable of binding to low-sulfated keratan sulfate.

3. The method according to claim 1, wherein for the antibody, the epitope comprises Gal-GlcNAc (6S) or a tandem repeat thereof.

4. The method according to claim 1, wherein the culture supernatant or the lysate contains serum.

5. The method according to claim 1, comprising steps of:
   contacting the culture supernatant or the lysate with the lectin to form a first complex composed of the lectin and podocalyxin contained in the culture supernatant or the lysate; and
   contacting the first complex with the antibody to form a second complex composed of the lectin, podocalyxin, and the antibody.

6. The method according to claim 5, wherein the lectin is bound to an insoluble support.

7. A method for detecting a stem cell by detecting a sugar chain represented by (Formula 1) below:

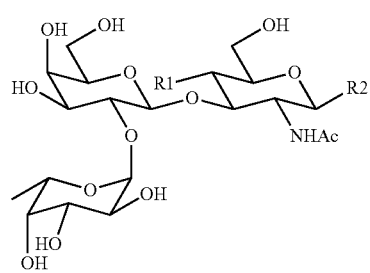
[Formula 3]

wherein R1 represents an OH group or any sugar chain and R2 represents an OH group or any sugar chain, protein, lipid, or another molecule,
or (Formula 2) below:

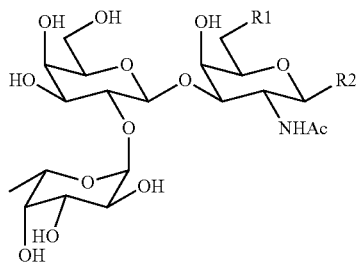
[Formula 4]

wherein R1 represents an OH group or any sugar chain and R2 represents an OH group or any sugar chain, protein, lipid, or another molecule, contained in a culture supernatant or a lysate of cells,
the method comprising steps of:
contacting the culture supernatant or the lysate,
   a lectin capable of binding to the sugar chain, wherein the lectin is:
a protein comprising the amino acid sequence of SEQ ID NO: 1 or
a protein comprising an amino acid sequence in which one amino acid is deleted, substituted, inserted, or added in the amino acid sequence of SEQ ID NO: 1 and being capable of binding to a sugar chain represented by the (Formula 1) or (Formula 2), and
   an antibody capable of binding to keratan sulfate, wherein the antibody is an antibody produced by hybridoma R-10G (accession number: FERM BP-11301),
   to form a complex comprising the lectin, the sugar chain, and the antibody; and
detecting the complex, wherein the detection of the complex is indicative of the presence of the stem cell.

8. The method according to claim 7, further comprising a step of determining the presence or absence or abundance of the stem cell contained among the cells based on the presence or absence or a detected amount of the complex.

9. The method according to claim 7, further comprising a step of determining the differentiation status of the cells based on the presence or absence or a detected amount of the complex.

10. A method for detecting podocalyxin contained in a culture supernatant or a lysate of cells, the method comprising steps of:
contacting the culture supernatant or the lysate,
   a lectin capable of binding to a sugar chain represented by (Formula 1) below:

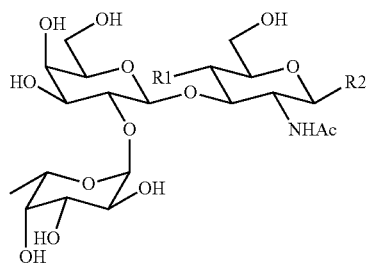
[Formula 5]

wherein R1 represents an OH group or any sugar chain and R2 represents an OH group or any sugar chain, protein, lipid, or another molecule,
or (Formula 2) below:

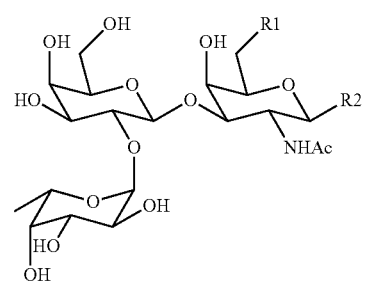
[Formula 6]

wherein R1 represents an OH group or any sugar chain and R2 represents an OH group or any sugar chain, protein, lipid, or another molecule, wherein the lectin is:
a protein comprising the amino acid sequence of SEQ ID NO: 1 or
a protein comprising an amino acid sequence in which one amino acid is deleted, substituted, inserted, or added in the amino acid sequence of SEQ ID NO: 1 and being capable of binding to a sugar chain represented by the (Formula 1) or (Formula 2), and
   an antibody capable of binding to keratan sulfate, wherein the antibody is an antibody produced by hybridoma R-10G (accession number: FERM BP-11301),
   to form a complex composed of the lectin, podocalyxin, and the antibody; and
detecting the complex, wherein the detection of the complex is indicative of the presence of podocalyxin.

11. A kit for detecting a stem cell contained among cells by detecting podocalyxin contained in a culture supernatant or a lysate of the cells, the kit comprising:
a lectin capable of binding to a sugar chain represented by (Formula 1) below:

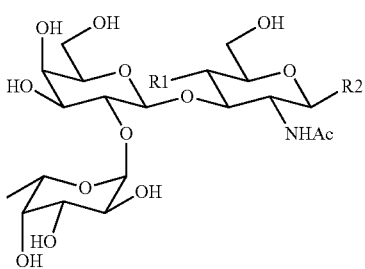

wherein R1 represents an OH group or any sugar chain and R2 represents an OH group or any sugar chain, protein, lipid, or another molecule,
or (Formula 2) below:

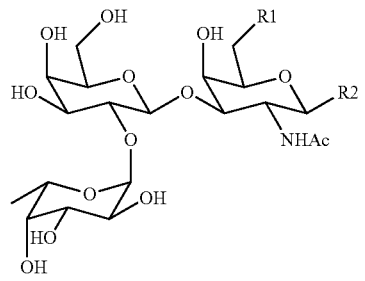

wherein R1 represents an OH group or any sugar chain and R2 represents an OH group or any sugar chain, protein, lipid, or another molecule, wherein the lectin is:

a protein comprising the amino acid sequence of SEQ ID NO: 1 or a protein comprising an amino acid sequence in which one amino acid is deleted, substituted, inserted, or added in the amino acid sequence of SEQ ID NO: 1 and being capable of binding to a sugar chain represented by the (Formula 1) or (Formula 2); and an antibody capable of binding to keratan sulfate, wherein the antibody is an antibody produced by hybridoma R-10G (accession number: FERM BP-11301).

12. The kit according to claim 11, wherein the antibody is an antibody capable of binding to low-sulfated keratan sulfate.

13. The kit according to claim 11, wherein for the antibody, the epitope comprises Gal-GlcNAc (6S) or a tandem repeat thereof.

14. The kit according to claim 11, wherein the lectin is bound to an insoluble support.

15. The method according to claim 1, further comprising a step of determining the presence or absence or abundance of the stem cell contained among the cells based on the presence or absence or a detected amount of the complex.

16. The method according to claim 1, further comprising a step of determining the differentiation status of the cells based on the presence or absence or a detected amount of the complex.

* * * * *

SEQUENCE LISTING

```
<160> NUMBER OF SEQ ID NOS: 2

<210> SEQ ID NO 1
<211> LENGTH: 156
<212> TYPE: PRT
<213> ORGANISM: Burkholderia cenocepacia

<400> SEQUENCE: 1

Met Pro Leu Leu Ser Ala Ser Ile Val Ser Ala Pro Val Val Thr Ser
1               5                   10                  15

Glu Thr Tyr Val Asp Ile Pro Gly Leu Tyr Leu Asp Val Ala Lys Ala
            20                  25                  30

Gly Ile Arg Asp Gly Lys Leu Gln Val Ile Leu Asn Val Pro Thr Pro
        35                  40                  45

Tyr Ala Thr Gly Asn Asn Phe Pro Gly Ile Tyr Phe Ala Ile Ala Thr
    50                  55                  60

Asn Gln Gly Val Val Ala Asp Gly Cys Phe Thr Tyr Ser Ser Lys Val
65                  70                  75                  80

Pro Glu Ser Thr Gly Arg Met Pro Phe Thr Leu Val Ala Thr Ile Asp
                85                  90                  95

Val Gly Ser Gly Val Thr Phe Val Lys Gly Gln Trp Lys Ser Val Arg
            100                 105                 110

Gly Ser Ala Met His Ile Asp Ser Tyr Ala Ser Leu Ser Ala Ile Trp
        115                 120                 125

Gly Thr Ala Ala Pro Ser Ser Gln Gly Ser Gly Asn Gln Gly Ala Glu
    130                 135                 140

Thr Gly Gly Thr Gly Ala Gly Asn Ile Gly Gly Gly
145                 150                 155

<210> SEQ ID NO 2
```

```
<211> LENGTH: 143
<212> TYPE: PRT
<213> ORGANISM: Agaricus bisporus

<400> SEQUENCE: 2

Met Thr Tyr Thr Ile Ser Ile Arg Val Tyr Gln Thr Thr Pro Lys Gly
1               5                   10                  15

Phe Phe Arg Pro Val Glu Arg Thr Asn Trp Lys Tyr Ala Asn Gly Gly
            20                  25                  30

Thr Trp Asp Glu Val Arg Gly Glu Tyr Val Leu Thr Met Gly Gly Ser
        35                  40                  45

Gly Thr Ser Gly Ser Leu Arg Phe Val Ser Ser Asp Thr Asp Glu Ser
    50                  55                  60

Phe Val Ala Thr Phe Gly Val His Asn Tyr Lys Arg Trp Cys Asp Ile
65                  70                  75                  80

Val Thr Asn Leu Thr Asn Glu Gln Thr Ala Leu Val Ile Asn Gln Glu
                85                  90                  95

Tyr Tyr Gly Val Pro Ile Arg Asp Gln Ala Arg Glu Asn Gln Leu Thr
            100                 105                 110

Ser Tyr Asn Val Ala Asn Ala Lys Gly Arg Arg Phe Ala Ile Glu Tyr
        115                 120                 125

Thr Val Thr Glu Gly Asp Asn Leu Lys Ala Asn Leu Ile Ile Gly
    130                 135                 140
```